(12) United States Patent
Adams et al.

(10) Patent No.: US 6,833,251 B2
(45) Date of Patent: Dec. 21, 2004

(54) BACTERIA DETECTION USING IMMOBILIZED ENZYME SUBSTRATES

(75) Inventors: Carl A. Adams, Apple Valley, MN (US); Gary E. Krejcarek, White Bear Lake, MN (US); James H. Wicks, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 294 days.

(21) Appl. No.: 10/160,594

(22) Filed: May 30, 2002

(65) Prior Publication Data

US 2003/0017449 A1 Jan. 23, 2003

Related U.S. Application Data

(63) Continuation of application No. 09/548,157, filed on Apr. 13, 2000, now Pat. No. 6,436,661.

(51) Int. Cl.$^7$ ................................................. C12Q 1/04
(52) U.S. Cl. ........................... 435/34; 435/30; 435/180; 435/259
(58) Field of Search .............................. 435/259, 34, 5, 435/6, 30, 39, 180

(56) References Cited

U.S. PATENT DOCUMENTS

| | | | |
|---|---|---|---|
| 4,029,597 A | 6/1977 | Neisius et al. | |
| 4,104,126 A | 8/1978 | Young | |
| 4,565,783 A | 1/1986 | Hansen et al. | |
| 4,861,709 A | 8/1989 | Ulitzur et al. | |
| 5,089,413 A | 2/1992 | Nelson et al. | |
| 5,232,838 A | 8/1993 | Nelson et al. | |
| 5,238,809 A | 8/1993 | Wolfbeis | |
| 5,292,840 A | 3/1994 | Heilmann et al. | |
| 5,498,525 A | 3/1996 | Rees et al. | |
| 5,561,097 A | 10/1996 | Gleason et al. | |
| 5,601,998 A | 2/1997 | Mach et al. | |
| 5,723,308 A | 3/1998 | Mach et al. | |
| 5,763,251 A | 6/1998 | Gasson | |
| 5,888,725 A | 3/1999 | Sanders | |
| 5,914,240 A | 6/1999 | Sanders | |
| 5,958,675 A | 9/1999 | Wicks et al. | |
| 5,985,596 A | 11/1999 | Wilson | |
| 5,998,593 A | 12/1999 | Huff et al. | |
| 6,080,423 A | 6/2000 | Charych et al. | |
| 6,251,624 B1 | 6/2001 | Matsumura et al. | |
| 6,436,661 B1 * | 8/2002 | Adams et al. | ................. 435/34 |

FOREIGN PATENT DOCUMENTS

| | | |
|---|---|---|
| DE | 196 17 338 A1 | 11/1997 |
| EP | 0 313 274 | 4/1989 |
| EP | 0 519 198 A2 | 12/1992 |
| WO | WO 93/07483 | 4/1993 |
| WO | WO 96/06183 | 2/1996 |

OTHER PUBLICATIONS

Rabina et al., "A Time–Resolved Immunofluorometric Method for the Measurement of Sialyl Lewis x–Synthesizing α 1,3–Fucosyltransferase Activity," Analytical Biochemistry vol. 246, No. 1, 1997, pp. 71–78.

Excerpt: Mar. "Advanced Organic Chemistry," *Wiley InterScience*, 4$^{th}$ Edition, 1992, pp. 420–421.

Blasco R., "Specific Assays for Bacteria Using Phage Mediated Release of Adenylate Kinase," *J. of Applied Microbiology* 84(4)661–686, Apr. 1998.

* cited by examiner

*Primary Examiner*—Ralph Gitomer
(74) *Attorney, Agent, or Firm*—Christopher D. Gram; Robert W. Sprague

(57) ABSTRACT

Methods of detecting bacteria including the use of an immobilized enzyme substrate are provided.

13 Claims, No Drawings

BACTERIA DETECTION USING IMMOBILIZED ENZYME SUBSTRATES

This application is a continuation of U.S. patent application Ser. No. 09/548,157, filed Apr. 13, 2000, now U.S. Pat. No. 6,436,661.

BACKGROUND OF THE INVENTION

Detection of bacteria is important in a variety of industries, including the food and beverage industry. For example, the need to screen food and water for pathogenic bacteria is crucial to ensuring consumer safety. The determination of levels of certain families of bacteria is a commonly used approach to estimating the shelf life and microbial acceptability of food products and hygienic status of the processing equipment and raw materials used in their manufacture. The diagnosis of microbial infections also relies on the detection of the causative organism(s).

There are many methods known for detecting bacteria. For example, bacteriophage, which are viruses that infect bacteria, may be employed. The presence of the bacteriophage, the infected bacteria, or the lack thereof, may be detected. Typically, a target bacteria is detected by infecting the bacteria with a bacteriophage (BP) specific to the bacteria, inactivating the excess BP, and then manipulating the BP-infected bacteria in some manner to detect the presence or absence of the BP as an indirect indication of whether or not the sample originally contained the target bacteria. Bacterial "helper cells" can be used to amplify the number of BP-infected bacteria and thereby enhance, e.g., make more rapid, the assay method. A common detection method in the final stages of such an assay is to incubate the bacterial helper cells with the BP-infected bacteria and either observe changes in solution turbidity or, alternatively, observe BP plaque formation on an appropriate growth medium.

For example, U.S. patent application Ser. No. 09/434,586 (Wicks et al.) describes devices and methods for the detection of bacteria in a sample. Briefly, a sample containing suspect (target) bacteria is infected with a BP specific to the suspect bacteria, the excess BP is inactivated with an antiviral agent, and the BP-infected bacteria are added to bacterial helper cells to amplify the BP and to produce a signal that can be detected visually or with an instrument. For example, the BP can be detected by incubating the helper cells on agar and counting the number of BP plaques that are formed.

It would be very useful in such assay methods to employ enzyme substrates (ES) as indicators for detecting the presence of BP (and, thus, indirectly the presence or absence of target bacteria). Utilizing ES indicators could lead to significant advantages over trying to observe changes in solution turbidity or counting plaque formation. The use of ES indicators could lead to more convenient, more rapid, and less expensive assay methods. However, the use of traditional soluble ES indicators is generally not possible in such assay methods. The soluble ES would undesirably react with enzyme within the intact bacteria cells of both non-target bacteria and, if used, bacterial helper cells and thereby produce unacceptable levels of background signal.

SUMMARY OF THE INVENTION

The present invention solves the problem of the prior art by utilizing enzyme substrates as indicators that have been bonded (i.e., immobilized) to an insoluble solid support. The use of an immobilized enzyme substrate prevents the enzyme substrate from crossing a bacteria cell wall to react with enzyme within intact bacteria cells. As a result, the enzyme substrate can only react with an enzyme released from a lysed bacteria cell.

The present invention provides a method of detecting (identifying and/or quantifying) target bacteria. The method includes: combining bacteriophage and a sample of interest to form a reaction mixture; incubating the reaction mixture under conditions effective for the bacteriophage to lyse any target bacteria present in the sample of interest and release enzyme; adding an immobilized enzyme substrate to the reaction mixture; and monitoring the reaction mixture for a detectable signal produced from interaction between the immobilized enzyme substrate and any released enzyme present. Adding the immobilized enzyme substrate to the reaction mixture can occur before or after incubating the reaction mixture. This method can involve a qualitative or quantitative determination of bacteria in a sample.

In a preferred embodiment, the present invention provides a method of detecting target bacteria that involves: combining bacteriophage and a sample of interest to form a reaction mixture; allowing the bacteriophage to infect any target bacteria present in the sample of interest; adding an antiviral agent to inactivate any extracellular bacteriophage; adding bacterial helper cells to the reaction mixture; adding an immobilized enzyme substrate to the reaction mixture; incubating the reaction mixture under conditions effective for the bacteriophage to lyse any target bacteria present and the bacterial helper cells and release enzyme; and monitoring the reaction mixture for a detectable signal produced from interaction between the immobilized enzyme substrate and any released enzyme present. This method is preferably used for the quantitative determination of bacteria in a sample, although it can also involve a qualitative determination.

The present invention also provides an immobilized enzyme substrate that includes a porous solid support and an enzyme substrate covalently bonded thereto.

DETAILED DESCRIPTION OF ILLUSTRATIVE EMBODIMENTS OF THE INVENTION

The present invention provides a method of detecting the presence or absence of bacteria using an immobilized enzyme substrate (i.e., enzyme reactant). Thus, the present invention provides a method that uses enzyme activity for the detection of bacteriophage, which provides an indirect method for the detection of bacteria, or for the detection of bacteria directly.

The enzyme substrate preferably includes a detectable label that, upon contact with enzyme present in the sample to be tested, produces a change, for example, in the spectral properties of the enzyme substrate or its reaction products resulting from the enzyme reaction. This change is used for the determination of the enzyme activity, and hence, the presence or absence of bacteriophage, and hence bacteria, or bacteria directly. Preferably, the change is a spectral change in the fluorescence radiation of the enzyme substrate, although other spectral changes can be used such as changes in absorption or excitation, for example.

The enzyme substrate can be immobilized on a variety of solid supports. Preferably, it is a porous support, although other supports can be used such as an optical fiber, as disclosed in U.S. Pat. No. 5,238,809 (Wolfbeis). In this latter embodiment, the enzyme substrate is attached to the end of an optical fiber and a photodetector for subsequent signal evaluation is provided, which will measure the signal, e.g., fluorescent light, emitted by the enzyme substrate or its reaction products, upon reaction with an enzyme. Suitable photodetectors are photomultipliers, phototransistors and photodiodes. Preferably, the optical fiber is a single fiber, but it may also be configured as a multi-fiber bundle.

Solid Support

Acceptable supports for use in the present invention can vary widely. A support can be porous or nonporous, but is preferably porous. It can be continuous or noncontinuous, flexible or nonflexible. A support can be made of a variety of materials including supports made of ceramic, glassy, metallic, organic polymeric materials, or combinations thereof. Such supports can be magnetic, which allows for concentration and intensification of the signal.

Preferred supports include organic polymeric supports, such as particulate or beaded supports, woven and nonwoven webs (such as fibrous webs), microporous fibers, microporous membranes, hollow fibers or tubes. Woven and nonwoven webs may have either regular or irregular physical configurations of surfaces.

Porous materials are particularly desirable because they provide large surface areas. The porous support can be synthetic or natural, organic or inorganic. Suitable solids with a porous structure having pores of a diameter of at least about 1.0 nanometer (nm) and a pore volume of at least about 0.1 cubic centimeter/gram ($cm^3/g$). Preferably, the pore diameter is at least about 30 nm because larger pores will be less restrictive to diffusion. Preferably, the pore volume is at least about 0.5 $cm^3/g$ for greater potential capacity due to greater surface area surrounding the pores. Preferred porous supports include particulate or beaded supports.

For significant advantage, the supports are preferably hydrophilic, and have high molecular weight (preferably, greater than about 5000, and more preferably, greater than about 40,000). Preferably, the hydrophilic polymers are water swellable to allow for greater infiltration of enzyme. Examples of such supports include cellulose, modified celluloses, agarose, polyvinyl alcohol (PVA), dextrans, amino-modified dextrans, polyacrylamide, modified guar gums, guar gums, xanthan gums, and locust bean gums.

In order to be useful for the purposes of the invention, the support includes a reactive functional group that can be used for coupling to the enzyme substrate, preferably through a spacer group. Preferably, the reactive functional group is capable of undergoing rapid, direct, covalent coupling with the desired spacer group to form derivatized supports. Preferably, the support includes at least one reactive functional group, such as a hydroxyl, carboxyl, sulfhydryl, or amino group that chemically binds to the enzyme substrate, optionally through a spacer group. Other suitable functional groups include N-hydroxysuccinimide esters, sulfonyl esters, iodoacetyl groups, aldehydes, imidazolyl carbamates, and cyanogen bromide activated supports. Such functional groups can be provided to a support by a variety of known techniques. For example, a glass surface can be derivatized with aminopropyl triethoxysilane in a known manner.

Coupling agents are preferably used in bonding the enzyme substrate to a support. For example, the coupling agents EDC (1-(3-dimethylaminopropyl)-3-ethyl carbodiimide hydrochloride) and HOBt (1-hydroxy-benzotriazole hydrate) can aid in covalently bonding a carboxyl group of the enzyme substrate to an amino group of an amino-modified support. The use of such coupling agents is described in *Advanced Organic Chemistry*, Jerry March, Wiley InterScience, 4$^{th}$ Edition, 1992, pp 420–421.

Spacer groups can also be used for bonding the enzyme substrate to a support. Suitable spacer groups include long-chain diamines, such as hexamethylene diamine.

Immobilization of an enzyme substrate to a support can also occur electrostatically (i.e., ionically), although covalent attachment is preferred. For example, immobilization can occur through the interaction between the negatively charged sulphonate groups of an enzyme substrate (e.g., one derivitized with 1-hydroxypyrene-3,6,8-trisulphonate) and positively charged surface ammonium groups of an anion exchanger used as a solid support.

Particularly preferred reactive supports useful in the present invention are supports having azlactone-functional groups on internal and/or external surfaces of such supports. Such reactive groups have an azlactone-functional group of the following formula:

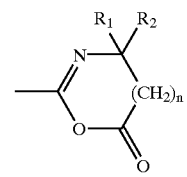

wherein $R_1$ and $R_2$ are independently a (C1–C14) alkyl group, a (C3–C14) cycloalkyl group, a (C5–C12) aryl group, a (C6–C26) arenyl group optionally having up to three S, N, and nonperoxidic O heteroatoms, or $R_1$ and $R_2$ taken together with the carbon to which they are joined can form a carbocyclic ring containing 4–12 ring atoms, and n=0 or 1.

Azlactone-functional reactive supports are particularly preferred because they are generally stable. They also rapidly and directly covalently couple enzyme substrates, optionally with spacer groups, better and with fewer side reactions (e.g., hydrolysis) than other supports having reactive functional groups. Furthermore, they possess high covalent coupling capacities with nucleophiles. Azlactone-functional reactive supports can be made by a number of methods as disclosed in U.S. Pat. No. 5,561,097 (Gleason et al.).

Enzyme Substrates

A wide variety of enzyme substrates (ES) can be used. Preferably, the enzyme substrates include a group capable of interacting with, or more preferably reacting with, the hydroxyl, amino, or sulfhydryl moiety, for example, of a solid support such that the reaction results in the bonding of the ES to the support. Preferably, the mechanism of bonding to the support does not interfere with the ability of the enzyme to act on the ES or destroy the ability of the ES to produce a signal when acted upon by the enzyme.

Enzyme substrates include those that interact with enzymes to give a detectable signal. Examples include, but are not limited to, enzyme substrates for beta-galactosidase (beta-gal), beta-glucuronidase, alcohol dehydrogenase or other NAD oxidoreductases, transferases, alkaline phosphatases or other hydrolases, lyases, isomerases, oxidases, gyrases, nucleases (DNases and RNases), and restriction enzymes. Such enzymes are produced by bacteria. Enzyme substrates typically can be polypeptides, carbohydrates (e.g., polysaccharides), or fatty acid derivatives.

A suitable enzyme substrate preferably includes a detectable label. Examples of such labels include fluorescent, luminescent, and chromogenic labels. Preferred labels are fluorescent. Examples of fluorescent labels include coumarin, fluorescein and fluorescein derivatives. Examples of lumiescent labels include adamantyl oxirane derivatives. Examples of chromogenic labels include sulphonphthaleins, sulphonphthalein derivatives, and indoxyl compounds and their derivatives.

Specific examples of enzyme substrates include coumarin-4-acetic acid 7-O-caprylate, coumarin-4-acetic acid 7-O-beta-D-glucuronide, and coumarin-4-acetic acid 7-O-beta-D-galactopyranoside The immobilization of coumarin-4-acetic acid 7-O-beta-D-galactopyranoside via an azlactone-functionalized solid support has the following structure (wherein "B-D- refers to "beta-D"):

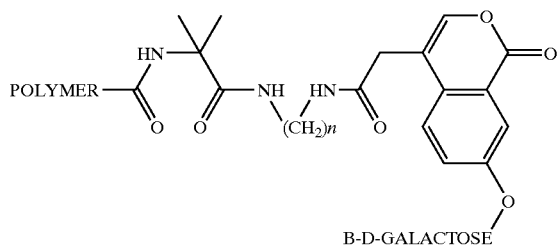

The immobilized dye resulting from this process is a synthetic reactant for dealkylases (such as galactosidase). Such enzymes will split the ether groups, thereby producing a signal from the immobilized fluorescent dye 7-hydroxy-coumarin-4-acetic acid (i.e., a derivative of the acetic acid-functional dye), which may be detected.

Not only synthetic enzyme substrates, but also naturally occurring enzyme substrates labeled with a dye can be immobilized on a solid support. For example, egg albumin lysozyme can be immobilized on a solid support and then labeled with a fluorescent dye, e.g., fluoresceinisothiocyanate. Upon contact with the enzyme trypsin this enzyme substrate will decompose releasing fluorescein and fluorescein-marked fragments of the lysozyme.

Bacteria and Bacteriophages

The type of bacteria that can be detected using the method and immobilized enzyme substrate of the present invention is not limited. Suitable target bacteria that can be hosts for bacteriophage and detectable according to the present invention include, but are not limited to, those of the following genera: *Escherichia, Enterobacter, Salmonella, Staphylococci, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campybacter, Vibrio, Serratia, Providencia, Chromobacterium, Brucella, Yersinia, Haemophilus, Bivrio,* and *Bordetella*. Such bacteria can also be used as reagents in methods of the present invention.

Bacteriophage that may be used in a method according to the present invention is not limited. Suitable bacteriophage that can interact with target bacteria or bacterial helper cells include but are not limited to *Escherichia* phage, *Enterobacter* phage, *Salmonella* phage, *Staphylococci* phage, *Shigella* phage, *Listeria* phage, *Aerobacter* phage, *Klebsiella* phage, *Proteus* phage, *Pseudomonas* phage, *Streptococcus* phage, *Chlamydia* phage, *Mycoplasma* phage, *Pneumococcus* phage, *Neisseria* phage, *Clostridium* phage, *Bacillus* phage, *Corynebacterium* phage, *Mycobacterium* phage, *Campybacter* phage, *Vibrio* phage, *Serratia* phage, *Providencia* phage, *Chromobacterium* phage, *Brucella* phage, *Yersinia* phage, *Haemophilus* phage, *Bivrio* phage, and *Bordetella* phage. Such phage are typically available from the American Type Culture Collection (ATCC) or can be isolated from nature, and can be used in the form of lyophilized pellets, for example.

A wide variety of enzymes are produced upon the lysis of bacterial cells using bacteriophage. The released enzyme reacts with an immobilized enzyme substrate to give a detectable signal. Examples include, but are not limited to, beta-galactosidase (beta-gal), beta-glucuronidase, alcohol dehydrogenase or other NAD oxidoreductases, transferases, alkaline phosphatases or other hydrolases, lyases, isomerases, oxidases, gyrases, nucleases (DNases and RNases), and restriction enzymes.

Conditions effective for such lysis to occur are generally well known to one skilled in the art. Such conditions are disclosed in E. L. Ellis et al., "The growth of bacteriophage," *J. Gen. Physiol.*, 22, 365 (1939), and typically include sufficient time at a temperature of about 37° C. under conditions suitable for bacterial growth.

Types of Assay

The method and immobilized enzyme substrate of the present invention can be used in a variety of assays. The immobilized enzyme substrate can be added with bacteriophage to a sample of interest for detecting a target bacteria. The bacteriophage chosen is one that will infect and subsequently lyse the bacteria of interest.

In one embodiment, a method of detecting target bacteria includes: combining bacteriophage and a sample of interest to form a reaction mixture; incubating the reaction mixture under conditions effective for the bacteriophage to lyse any target bacteria present in the sample of interest and release enzyme; adding an immobilized enzyme substrate to the reaction mixture; and monitoring the reaction mixture for a detectable signal produced from interaction between the immobilized enzyme substrate and any released enzyme present. Adding the immobilized enzyme substrate to the reaction mixture can occur before or after incubating the reaction mixture.

Bacteria detection methods according to the present invention can involve a qualitative or quantitative determination. For a quantitative determination of bacteriophage, for example, the reaction mixture can be plated out on an appropriate growth medium, and the areas emitting the detectable signal are counted. Such areas typically become plagues (i.e., areas of clearing or bacteriophage-derived discontinuity on a lawn of bacterial "helper cells") with sufficient time. A standard test method for plaque detection is described in Standard Test Method for Coliphages in Water, ASTM Designation: D4201-82 (Reapproved 1989).

Preferably, a quantitative assay for bacteria involves phage amplification to detect bacteria by observing the formation of plaques. Generally, this method involves: combining bacteriophage and a sample of interest to form a reaction mixture; allowing the bacteriophage to infect any target bacteria present in the sample of interest; adding an antiviral agent to inactivate any extracellular bacteriophage; adding bacterial helper cells to the reaction mixture; adding an immobilized enzyme substrate to the reaction mixture; incubating the reaction mixture under conditions effective for the bacteriophage to lyse any target bacterium present and the bacterial helper cells and release enzyme; and monitoring the reaction mixture for a detectable signal produced from interaction between the immobilized enzyme substrate and any released enzyme present. If no target bacteria are present, the bacteriophage will be all inactivated by the antiviral agent and no lysing of the bacterial helper cells will occur. This method is preferably used for the quantitative determination of bacteria in a sample, although it can also involve a qualitative determination.

The immobilized ES would react with the bacterial enzyme released by bacteriophage infection of the target bacteria and subsequent breaking (lysis) of the cell wall, but the immobilized ES would not cross a bacteria cell wall to react with enzyme still within intact bacteria cells. Therefore, an immobilized ES could be utilized in the final stages of an assay to produce a signal indicating the presence of target bacteria in the original sample with little or no interference from bacteria "helper cells" or non-target bacteria.

Suitable bacterial helper cells can be the same or different than the target bacteria. Preferably, they are closely related to the target bacteria such that they can be infected by the chosen bacteriophage. Examples of bacterial helper cells include those listed above for the target and reagent bacteria.

The phage amplification can occur on a wide variety of culture media known to one of skill in the art. Typically, a culture media includes various nutrients, including a carbon source such as a carbohydrate, and a nitrogen source such as an amino acid or protein hydrolysate. Alternatively, the amplification can occur on a solid or semi-solid culture device such as a "PETRILM" device as disclosed in U.S. Pat. No. 5,958,675 (Wicks et al.)

Also, the method and immobilized enzyme substrate can be incorporated into the device disclosed in U.S. patent application Ser. No. 09/434,586 (Wicks et al.) filed on Nov. 5, 1999, which includes at least two chambers separated by an activatable seal (i.e., a component, such as a valve, that separates two compartments so as to prevent leakage) wherein upon activation of the seal, the two chambers are in communication. Preferably, this device is in the form of a tube, which can have a variety of cross-sectional shapes, although other constructions (e.g., rectangular or circular tubes, channels on a flat substrate, or microreplicated structures) are envisioned.

In a preferred embodiment, the device is used in the detection of bacteria (target bacteria) by adding bacteriophage to a test sample to infect the target bacteria in the test sample, killing the extracellular bacteriophage with an antiviral (or mixture of antivirals, such as ferrous salts, cuprous salts, leaf extracts, pomegranate rind extracts, and organic acids, suitable for killing extracellular bacteriophage), neutralizing the antiviral (for example, with a buffer), adding an immobilized ES, and amplifying the bacteriophage by incubating the resulting mixture in the presence of a lawn of bacterial helper cells. Such phage amplification assays that use plaque formation as the end-point (and no ES) are known to those of skill in the art and are disclosed in U.S. Pat. No. 5,498,525 (Rees et al.). In the presence of an immobilized ES, such as described in Example 4 of the present invention, the appearance of a fluorescent signal is an indication that the test sample contained the target bacteria. The assay results in the form of a fluorescent signal can be read rapidly, typically within about four hours to about six hours, and confirming at 24 hours, if needed. Conventional methods to enumerate bacteria usually require about 24 hours to about 48 hours of growth.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

Example 1

Enzyme Substrate Bonded to an Insoluble Support

The objective of this experiment was to prepare an enzyme substrate (coumarin-4-acetic acid 7-O-beta-D-galactopyranoside) covalently bonded to an insoluble support substance (azlactone beads).

A sample (10 g) of azlactone beads (Pierce Chemical Co., Rockford, Ill.) was derivatized with 1,6-hexanediamine (as described in Example 11 of U.S. Pat. No. 5,561,097) to provide a free amino group at each azlactone site. Approximately 41 mmole amine equivalents were used per ml of azlactone beads suspension. A sample (200 mg) of the derivatized azlactone beads was added to a solution of the fluorogenic substrate coumarin-4-acetic acid 7-O-beta-D-galactopyranoside (10 mg, Sigma, St. Louis, Mo.), dicyclohexyl carbodiimide (DCC) (5.4 mg, Aldrich Chemical, Milwaukee, Wis.), and 1-hydroxybenzotriazole (HOBt) (7 mg, Aldrich Chemical) all in DMF to provide a total volume of 3 ml. The resulting mixture was constantly agitated in a laboratory tube rocker for five days at room temperature. The supernatant liquid was discarded and the beads were washed with copious amounts of water and were resuspended in water (1 ml). The resulting suspension showed very little fluorescence and, after the suspension was centrifuged, all of the fluorescence was carried by the bead pellet. The supernatant liquid from the centrifugation did not give a fluorescent signal over background when the purified enzyme beta-galactosidase (beta-gal) was added. However, when beta-gal was added to the bead pellet resuspended in fresh buffer (Butterfield's buffer, Fisher Scientific, Pittsburgh, Pa.), a very strong fluorescent signal was observed.

Example 2

Enzyme Substrate Bonded to an Insoluble Support in the Presence of E. coli Cells and Bacteriophage The objective of this experiment was to observe the fluorescent signal produced from an enzyme substrate attached to an insoluble support in the presence of E. coli cells, both in the presence and absence of bacteriophage.

A sample (50 mg of beads) of the enzyme substrate coumarin-4-acetic acid 7-O-beta-D-galactopyranoside covalently bonded to the insoluble azlactone beads support (as described in Example 1) was added to Butterfield's buffer (1 ml, pH 7, Fisher Scientific) that contained E. coli 625 cells (Silliker Laboratories, Chicago Heights, Ill.) having an initial concentration of approximately $10^8$ cells/ml. The resulting mixture was incubated for 6–10 hours at 37° C. both in the presence and absence of bacteriophage RB33s ($10^6$ phage, T4 Laboratory, Evergreen State College, Olympia, Wash.) that was capable of lysing the E. coli cells. A sample of the substrate-beads in Butterfield's buffer medium only was also incubated in the same manner and showed little or no fluorescent signal. The incubated medium containing E. coli cells but no bacteriophage showed only a low background level of fluorescence. The incubated medium containing the E. coli cells and the bacteriophage showed a higher level of fluorescence. This higher level of fluorescence was attributed to the lysis of E. coli cells by the bacteriophage and the subsequent release of the residual beta-gal enzyme. The enzyme was then able to catalyze the hydrolysis of the beads-supported enzyme substrate to produce a hydrolysis product that emitted a highly fluorescent signal.

Example 3

Comparison of Bonded Substrate to Non-Bonded (Free) Substrate in the Presence of E. Coli Cells The objective of this experiment was to show that an enzyme substrate (coumarin-4-acetic acid 7-O-beta-D- galactopyranoside) covalently bonded to an insoluble support substance (azlactone beads) produces little or low levels of fluorescent signal relative to free coumarin-4-acetic acid 7-O-beta-D-galactopyranoside in solution.

A sample (about 200 mg of beads) of the enzyme substrate coumarin-4-acetic acid 7-O-beta-D-galactopyranoside covalently bonded to the insoluble azlactone beads support (as described in Example 1) was suspended in 500 µl of sterile water and then 100 µl of this suspension was added to each of 5 wells of a 96-well plate (Co-Star, V.W.R., Chicago, Ill.). The quantity of beads was chosen so that hydrolysis of the enzyme substrate would be expected to give a fluorescent signal of about 4000 relative fluorescent units (RFU). Other wells were filled with free coumarin-4-acetic acid 7-O-beta-D-galactopyranoside (50 µg/ml) and contained no beads. A 100-µl aliquot of either E. coli 650 or E. coli 651 cells (prepared by centrifuging 1 ml of an overnight culture of each bacterium, washing 2× with Butterfield's buffer, and resuspending in 500 µl of fresh Luria-Bertani (LB) Broth) was then added to the sample wells. The well plates were then incubated at 37° C. for up to 6 hours. Changes in the fluorescence of each well were determined using a Cambridge Instruments Model 7620 Fluorescent Microplate Reader (Cambridge Instruments, Boston, Mass.). Those wells containing beads with covalently bound enzyme substrate gave little or no fluorescence while those that contained the free enzyme substrate in solution showed a marked increase in fluorescent signal (see Table 1).

TABLE 1

| Sample | E. Coli Strain | Fluorescence (RFU)[1] at Indicated Time (Hours) | | | |
|---|---|---|---|---|---|
| | | 0 | 1.5 | 2.5 | 4 |
| Free Enzyme Substrate | 560 | 161 | 226 | 337 | 717 |
| | 561 | 156 | 300 | 436 | 592 |
| Bonded Enzyme Substrate | 560 | 155 | 153 | 157 | 166 |
| | 561 | 148 | 170 | 160 | 175 |

[1]Each data point represents the average of 5 replicates.

Example 4

Detection of Bacteria Utilizing an Immobilized Enzyme Substrate

A phage amplification device (PAD) having separate chambers A, B, C, and D is constructed as described in Example 3 of U.S. patent application Ser. No. 09/434,586 (Wicks et al.). Center chambers B and C contain antiviral components. Following construction, a pellet of lyophilized E. coli, ATCC 13706 bacteria (approximately $1 \times 10^8$ cfu/ml) is added to Chamber D to serve as bacteria "helper cells". Additionally, a sample (50 mg of beads) of the enzyme substrate coumarin-4-acetic acid 7-O-beta-D-galactopyranoside covalently bonded to the insoluble azlactone beads support (as described in Example 1) is added to Chamber D. Chamber A is left empty to receive the test sample and all valves are set initially in a "closed position."

An overnight culture of E. coli, ATCC 13706 containing $1 \times 10^8$ cfu/ml is diluted ten-fold stepwise in Lambda buffer (as described in Example 4 of U.S. Pat. No. 5,498,525 (Rees et al.)) so that Chamber A of the PAD contains approximately 0.1 ml of culture solution. To this sample is added 10 µl of a Nutrient Broth (Product No. 4311479, BBL, Cockysville, Md.) suspension of bacteriophage [Phi X 174 (ATCC 13706-B 1)] containing $1 \times 10^{11}$ pfu/ml. The bacteriophage is allowed to adsorb to the bacteria cells for 10 minutes at 37° C. in an incubator. Valve 1 (between Chambers B and C) is then opened and the antiviral components of Chambers B and C are allowed to mix for 2 minutes at 23° C. Non-adsorbed bacteriophage is then inactivated by opening Valve 2 (between Chambers A and B) and allowing the antiviral solution to mix with the contents of Chamber A for 5 minutes at 23° C. The resulting solution is then neutralized by opening Valve 3 (between Chambers C and D) and combining the solution with the bacteria "helper cells" pellet and immobilized enzyme substrate in Chamber D for 5 minutes at 23° C. The PAD is then incubated at 23° C. for up to 6 hours and changes in fluorescence are determined. The fluorescent signal is an indication of E. coli bacteria in the original culture.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of detecting target bacteria, the method comprising:
   combining bacteriophage and a sample to form a reaction mixture;
   incubating the reaction mixture under conditions effective for the bacteriophage to lyse any target bacteria present in the sample, thereby releasing enzyme;
   adding to the reaction mixture an immobilized enzyme substrate ionically coupled to a solid support;
   allowing at least a portion of the immobilized enzyme substrate to react with enzyme released by the lysed target bacteria but not react with enzyme within intact bacteria, the reaction between released enzyme and immobilized enzyme substrate producing a detectable signal; and
   detecting the detectable signal.

2. The method of claim 1 wherein adding an immobilized enzyme substrate to the reaction mixture occurs prior to incubating the reaction mixture.

3. The method of claim 1 wherein detecting the detectable signal comprises quantitatively determining the amount of target bacteria present in the sample.

4. The method of claim 1 wherein the enzyme substrate is coumarin-4-acetic acid 7-O-caprylate, coumarin-4-acetic acid 7-O-beta-D-glucuronide, or coumarin-4-acetic acid 7-O-beta-D-galactopyranoside.

5. The method of claim 1 wherein the bacteriophage are Escherichia phage, Enterobacter phage, Salmonella phage, Staphylococcus phage, Shigella phage, Listeria phage, Aerobacter phage, Klebsiella phage, Proteus phage, Pseudomonas phage, Streptococcus phage, Chlamydia phage, Mycoplasma phage, Pneumococcus phage, Neisseria phage, Clostridium phage, Bacillus phage, Corynebacterium phage, Mycobacterium phage, Campylobacter phage, Vibrio phage, Serratia phage, Providencia phage, Chromobacterium phage, Brucella phage, Yersinia phage, Haemophilus phage, or Bordetella phage.

6. The method of claim 1 wherein the detectable signal is a fluorescent signal, luminescent signal, or chromogenic signal.

7. The method of claim 6 wherein the detectable signal is a fluorescent signal.

8. The method of claim 1 wherein the enzyme substrate comprises a negative charge and is ionically coupled to positively charged group on the solid support.

9. The method of claim 8 wherein the enzyme substrate is derivatized with 1-hydroxypyrene-3,6,8-trisulphonate.

10. The method of claim 8 wherein the solid support comprises ammonium groups.

11. A method of detecting target bacteria, the method comprising:
   combining bacteriophage and a sample to form a reaction mixture;
   allowing the bacteriophage to infect any target bacteria present in the sample;
   adding an antiviral agent to inactivate any extracellular bacteriophage;
   adding bacterial helper cells that are capable of being infected by the bacteriophage to the reaction mixture;
   incubating the reaction mixture under conditions effective for the bacteriophage to lyse infected target bacteria and infected bacterial helper cells, thereby releasing enzyme;
   adding to the reaction mixture an immobilized enzyme substrate ionically coupled to a solid support;
   allowing at least a portion of the immobilized enzyme substrate to react with enzyme released by the lysed bacteria but not react with enzyme within intact bacteria, the reaction between released enzyme and immobilized enzyme substrate producing a detectable signal; and
   detecting the detectable signal.

12. The method of claim 11 wherein detecting the detectable signal comprises quantitatively determining the amount of target bacteria present in the sample.

13. The method of claim 12 wherein quantitatively determining the amount of target bacteria present in the sample comprises plating the reaction mixture of the bacterial helper cells, immobilized enzyme substrate, and sample on a growth medium, and counting areas emitting the detectable signal.

* * * * *

UNITED STATES PATENT AND TRADEMARK OFFICE
CERTIFICATE OF CORRECTION

PATENT NO.   : 6,833,251 B2
DATED        : December 21, 2004
INVENTOR(S)  : Adams, Carl A.

It is certified that error appears in the above-identified patent and that said Letters Patent is hereby corrected as shown below:

Column 5,
Line 2, after "galactopyranoside" insert -- . --.

Column 7,
Line 16, delete "PETRILM" and insert in place thereof -- PETRIFILM --.

Signed and Sealed this

Twelfth Day of April, 2005

JON W. DUDAS
*Director of the United States Patent and Trademark Office*